(12) United States Patent
Asari et al.

(10) Patent No.: US 6,436,911 B1
(45) Date of Patent: Aug. 20, 2002

(54) IL-12 PRODUCTION INHIBITOR

(75) Inventors: Akira Asari, Iruma; Hitoshi Kurihara, Musashimurayama, both of (JP); Heping Xu, Scotland (GB); Satoshi Miyauchi, Musashimurayama; Toshikazu Minamisawa, Tokorozawa, both of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/620,747

(22) Filed: Jul. 21, 2000

(30) Foreign Application Priority Data

Jul. 21, 1999 (JP) ............................. 11-206586

(51) Int. Cl.[7] ...................... A01N 43/04; A61K 31/715; C07G 17/00; C07H 1/00; C07H 3/00
(52) U.S. Cl. ................... 514/53; 514/1; 514/23; 514/54; 514/61; 536/123; 536/123.1; 536/123.13
(58) Field of Search ................. 514/1, 23, 53, 514/54, 61; 536/123, 123.1, 123.13

(56) References Cited

U.S. PATENT DOCUMENTS

| | | | |
|---|---|---|---|
| 4,665,060 A | 5/1987 | Mårdh et al. | 514/61 |
| 4,851,338 A | 7/1989 | Mårdh et al. | 435/34 |
| 5,489,578 A | 2/1996 | Rosen et al. | 514/61 |
| 5,514,660 A | 5/1996 | Zopf et al. | 514/25 |
| 5,580,862 A | 12/1996 | Rosen et al. | 514/61 |
| 5,840,546 A | 11/1998 | Morikawa et al. | 435/71.1 |
| 5,874,411 A | 2/1999 | Srivastava et al. | 514/25 |
| 5,939,403 A | 8/1999 | Maruyama et al. | 514/53 |

FOREIGN PATENT DOCUMENTS

| | | |
|---|---|---|
| EP | 0 795 560 A1 | 9/1997 |
| WO | WO 91/06303 | 5/1991 |
| WO | WO 93/24506 | 12/1993 |
| WO | WO 96/16166 | 5/1996 |
| WO | WO 96/16973 | 6/1996 |

OTHER PUBLICATIONS

Gavin M. Brown, et al., Oligosaccharides Derived from Bovine Articular Cartilage Keratan Sulfates after Keratanase II Digestion: Implications for Keratan Sulfate Structural Fingerprinting, Biochemistry, vol. 3, No. 16, 1994 pp. 4836–4846.

Yoshio Itoh, et al., Syntheses of 2–Acetamido–2–deoxy–4–O–β–D–galactoyranosyl–D–glucopyranose (N–Acetyllactosamine) Derivatives, Chem. Pharm. Bull. 31(2), pp 727–729, 1983.

J. Drulović, et al. Serum interleukin–12 levels in patients with multiple sclerosis, Neuroscience Letters 251 (1998) 129–132.

Lazaros I. Sakkas, et al., Interleukin–12 Is Expressed by Infiltrating Macrophages and Synovial Lining Cells in Rheumatoid Arthritis and Osteoarthrities, Cellular Immunology 188, 105–110(1998).

*Primary Examiner*—Jezia Riley
(74) *Attorney, Agent, or Firm*—Knobbe, Martens, Olson and Bear, LLP

(57) ABSTRACT

An IL-12 production inhibitor which comprises, as an active ingredient, a keratan sulfate oligosaccharide or a derivative thereof, for example, a keratan sulfate oligosaccharide comprising at least one repeating unit of either one of the disaccharides represented by the following formulas: Gal (6s)-GlcNAc (6s) and Gal (6s)-GlcNAc wherein Gal represents a galactose residue, GlcNAc represents an N-acetylglucosamine residue, 6s indicates that 6-0-sulfate ester is formed at a Hydroxyl group at the 6-position, and - represents a glycosidic linkage.

8 Claims, 12 Drawing Sheets

MRL-*lpr/lpr*

IL-12 PRODUCTION INHIBITOR

BACKGROUND OF THE INVENTION

The present invention relates to an interleukin-12 (IL-12) production inhibitor and a keratan sulfate oligosaccharide derivative useful as an active ingredient of the IL-12 production inhibitor.

IL-12 is a cytokine composed of 70 kDa glycoprotein (p70) which is composed of linked two polypeptide chains of 35 kDa and 40 kDa and is known to play a pivotal role in the regulation of immune functions in living bodies (Shimpei Kasakura Ed., "Cytokine", Second Edition, Revised New Edition, pp. 207–225, Nihon Igakukan, Jun. 29, 1997).

It is also known that IL-12 induces differentiation of helper T cell type-1 subset (Th1) among T cells and hence accelerates progress of pathological conditions in autoimmune diseases associated with Th1 activation.

SUMMARY OF THE INVENTION

An object of the present invention is to provide an IL-12 production inhibitor that can effectively inhibit IL-12 production.

Another object of the present invention is to provide an active ingredient of the IL-12 production inhibitor.

The present inventors found that keratan sulfate oligosaccharides and derivatives thereof had an action to inhibit IL-12 production and thus accomplished the present invention.

The present invention provides an IL-12 production inhibitor (hereafter also referred to as the inhibitor of the present invention) which comprises a keratan sulfate oligosaccharide or a derivative thereof as an active ingredient.

The keratan sulfate oligosaccharide used in the inhibitor of the present invention preferably comprises at least one repeating unit of either one of the disaccharides represented by the following formulas:

Gal(6S)-GlcNAc(6S) and Gal(6S)-GlcNAc wherein, Gal represents a galactose residue, GlcNAc represents an N-acetylglucosamine residue, 6S indicates that 6-O-sulfate ester is formed at a hydroxyl group at the 6-position, and - represents a glycosidic linkage.

More preferably, the keratan sulfate oligosaccharide is selected from those represented by the formulas (1) to (3):

Gal(6S)β1-4GlcNAc(6S)β1-3Gal(6S)β1-4GlcNAc(6S)  (1)

Gal(6S)β1-4GlcNAc(6S)  (2)

Gal(6S)β1-4GlcNAc  (3)

wherein, Gal represents a galactose residue, GlcNAc represents an N-acetylglucosamine residue, 6S indicates that 6-O-sulfate ester is formed at a hydroxyl group at the 6-position, β1-4 represents a β-1,4-glycosidic linkage and β1-3 represents a β-1,3-glycosidic linkage.

The keratan sulfate oligosaccharide derivative used in the inhibitor of the present invention is preferably an acyl ester at a hydroxyl group of a keratan sulfate oligosaccharide, more preferably represented by the formula (4):

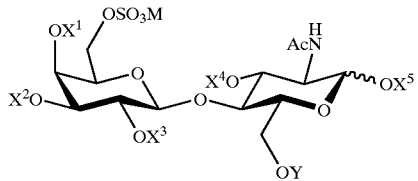

(4)

wherein, $X^1$ to $X^5$ each independently represent a hydrogen atom or an acyl group, provided that at least one of $X^1$ to $X^5$ is an acyl group; Y is a hydrogen atom or $SO_3M$; M is independently a hydrogen atom, or a monovalent to trivalent metal or a monovalent to trivalent base that may be ionized; the linkage represented by a wavy line represents a linkage in α-glycoside configuration or β-glycoside configuration.

Preferably, in the formula (4), each of $X^1$ to $X^5$ represents an acyl group having 1 to 10 carbon atoms and M is an alkali metal.

The present invention also provides a keratan sulfate oligosaccharide derivative represented by the above formula (4) (hereafter also referred to as the derivative of the present invention).

In the derivative of the present invention, it is preferred that each of $X^1$ to $X^5$ represents an acyl group having 1 to 10 carbon atoms and M is an alkali metal in the formula (4).

Furthermore, the present invention provide a pharmaceutical composition for inhibiting IL-12 production, comprising a keratan sulfate oligosaccharide or a derivative thereof and a pharmaceutically acceptable carrier. In addition, the present invention provide a method for inhibiting IL-12 production, comprising administering an effective amount of a keratan sulfate oligosaccharide or a derivative thereof to a subject in need of inhibition of IL-12 production, and a use of a keratan sulfate oligosaccharide or a derivative thereof for manufacture of a medicament for inhibiting IL-12 production.

The IL-12 production inhibitor is useful as a reagent for investigating the roles of IL-12 in the regulation of immune functions in living bodies. It can also be used as a therapeutic or prophylactic drug for diseases of which pathological conditions are accelerated by IL-12. The IL-12 production inhibitor of the present invention is highly safe because substances derived from nature are used as its material.

DETAILED DESCRIPTION OF THE INVENTION

Figure 1:
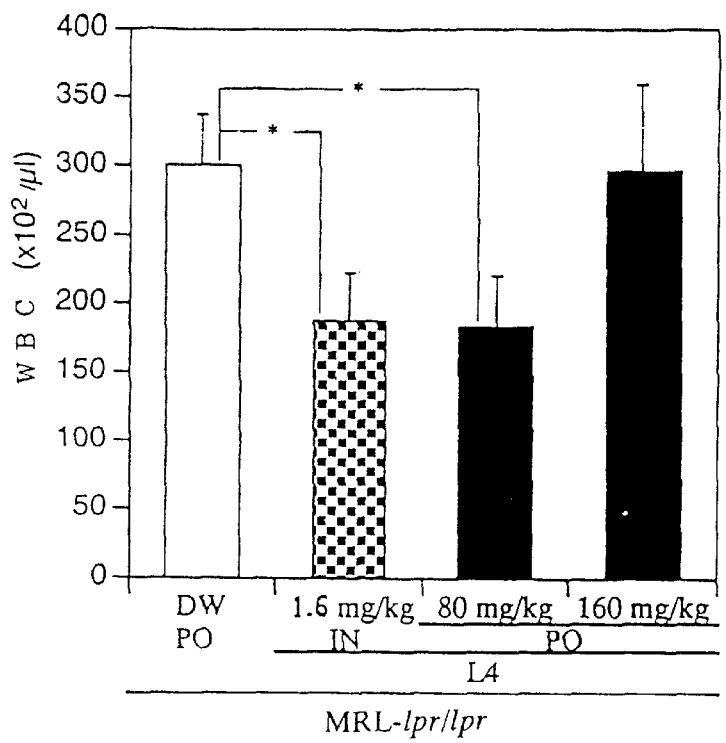
FIG. 1 shows counts of white blood cells (WBC) in blood of MRL-lpr/lpr mice after administration of L4.

The "keratan sulfate oligosaccharide" used in the inhibitor of the present invention are not limited so long as it is an oligosaccharide comprising two or more saccharides, containing at least the basic structure of keratan sulfate (a structure in which a galactose residue or galactose-6-O-sulfate residue and an N-acetylglucosamine residue or N-acetylglucosamine-6-O-sulfate residue are alternately linked through glycosidic linkage). The keratan sulfate oligosaccharide may be, for example, a product obtained by decomposing keratan sulfate, a product obtained by sulfating an oligosaccharide comprising one or more linked units of N-acetyllactosamine.

Among such keratan sulfate oligosaccharides, an oligosaccharide obtained by decomposing keratan sulfate (oligosaccharide derived from keratan sulfate) is preferred. A product obtained by decomposing keratan sulfate with a keratan sulfate-decomposing enzyme of endo-β-N-acetylglucosaminidase type is more preferred.

This keratan sulfate oligosaccharide may contain a sialic acid residue and/or a fucose residue. Usually, a sialic acid residue is linked to a galactose residue through α-2,3- or α-2,6-glycosidic linkage, and a fucose residue is linked to an N-acetylglucosamine residue through α-1,3-glycosidic linkage.

The keratan sulfate oligosaccharide is usually an oligosaccharide comprising 2 to 10 saccharides and having an N-acetylglucosamine residue at the reducing terminal. It does not matter whether the hydroxyl group at the 6-position of the N-acetylglucosamine residue is sulfated or not, but the hydroxyl group at the 6-position of a galactose residue is preferably sulfated.

More preferably, the keratan sulfate oligosaccharide contains at least one repeating unit of a disaccharide represented by Gal(6S)-GlcNAc(6S) or Gal(6S)-GlcNAc, wherein Gal represents a galactose residue, GlcNAc represents an N-acetyl glucosamine residue, 6S indicates that 6-O-sulfate ester is formed at a hydroxyl group at the 6-position, and —represents a glycosidic linkage.

Further preferably, the aforementioned keratan sulfate oligosaccharide is selected from an oligosaccharide represented by the formula (1) (hereafter also referred to as L4L4), an oligosaccharide represented by the formula (2) (hereafter also referred to as L4) and an oligosaccharide represented by the formula (3) (hereafter also referred to as L3):

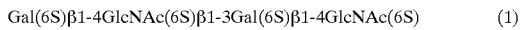

Gal(6S)β1-4GlcNAc(6S)β1-3Gal(6S)β1-4GlcNAc(6S)    (1)

Gal(6S)β1-4GlcNAc(6S)    (2)

Gal(6S)β1-4GlcNAc    (3)

wherein, Gal represents a galactose residue, GlcNAc represents an N-acetylglucosamine residue, 6S indicates that 6-O-sulfate ester is formed at a hydroxyl group at the 6-position, β1-4 represents a β-1,4-glycosidic linkage, and β1-3 represent a β-1,3-glycosidic linkage.

The keratan sulfate oligosaccharide used in the present invention include those ionized or protonated. They also include pharmaceutically acceptable salts of the keratan sulfate oligosaccharide.

In the present specification, a "derivative" of the keratan sulfate oligosaccharide means derivatives wherein at least one hydrogen atom of hydroxyl groups in the keratan sulfate oligosaccharide (preferably, 10% or more of all the hydroxyl groups) is replaced with an acyl group, preferably an O-acyl group (partially or completely O-acylated derivatives), and it includes pharmaceutically acceptable salts thereof.

The pharmaceutically acceptable salts include, but are not limited to, for example, pharmaceutically acceptable salts among alkali metal salts such as sodium salts, potassium salts and lithium salts, alkaline earth metal salt such as calcium salts, salts with an inorganic base such as ammonium salts and salts with an organic base such as diethanolamine salts, cyclohexylamine salts and amino acid salts.

The acyl group in a keratan sulfate oligosaccharide which substitutes for a hydrogen atom of hydroxyl group is preferably an acyl group having 1 to 10 carbon atoms, more preferably, an aliphatic or aromatic acyl group having 1 to 10 carbon atoms, that is, an alkanoyl group or aroyl group that may contain a hetero atom. Examples thereof include groups such as acetyl, chloroacetyl, dichloroacetyl, trifluoroacetyl, methoxyacetyl, propionyl, n-butyryl, (E)-2-methylbutenoyl, isobutyryl, pentanoyl, benzoyl, o-(dibromomethyl)benzoyl, o-(methoxycarbonyl)benzoyl, 2,4,6-trimethylbenzoyl, p-toluoyl, p-anisoyl, p-chlorobenzoyl and p-nitrobenzoyl. If the keratan sulfate oligosaccharide has a plurality of acyl groups, these acyl groups may be the same or different from each other.

If the hydrogen atom of the hydroxyl group at the 1-position in the reducing terminal saccharide of the keratan sulfate oligosaccharide is replaced with an acyl group, the configuration of the O-acyl group may be in α-glycoside configuration or β-glycoside configuration, but preferably in α-glycoside configuration.

Acylated keratan sulfate oligosaccharides have advantages such as improved solubility in organic solvents and lipids, increased permeability for biological membranes and increased absorption in the gastrointestinal tract when they are orally administered.

In the inhibitor of the present invention, the keratan sulfate oligosaccharide derivative is, preferably, one represented by the above formula (4). In the formula (4), M is independently a hydrogen atom, or a monovalent to trivalent metal atom or a monovalent to trivalent base that may be ionized. When ionized, the sulfonic acid group becomes a negative ion. More preferably, $X^1$ to $X^5$ all represents an acetyl group. A derivative represented by the following formula (5) is particularly preferred.

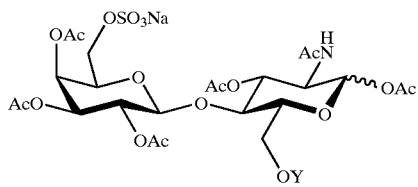

(5)

wherein, Ac represents an acetyl group; Y represents a hydrogen atom or SO₃Na; and the linkage represented by a wavy line represents a linkage in α-glycoside configuration or β-glycoside configuration.

The keratan sulfate oligosaccharide or a derivative thereof contained in the inhibitor of the present invention may be a single kind of substance or a mixture of substances. For example, it may be a purified product of a substance showing α-glycoside configuration at the linkage represented by a wavy line in the above formula (5), a purified product of a substance showing β-glycoside configuration at that linkage, or a mixture of these substances.

The keratan sulfate oligosaccharide used in the present invention can be obtained by allowing a keratan sulfate-decomposing enzyme of endo-β-N-acetylglucosaminidase type, for example, keratanase (II) derived from Bacillus bacteria (Japanese Patent Laid-open (Kokai) No. 2-57182/1990) or a keratan sulfate-decomposing enzyme derived form *Bacillus circulans* KsT202 strain (WO96/16166), to act on, for example, a buffer solution of keratan sulfate, preferably highly sulfated keratan sulfate, to decompose the keratan sulfate, and then fractionating the obtained decomposition product. The obtained oligosaccharides can be separated and purified by usual separation and purification methods such as, for example, ethanol precipitation, gel filtration and anion exchange chromatography, to obtain an objective oligosaccharide. Examples of these preparation methods are described in International Publication WO96/16973. Keratan sulfate used as a raw material is mainly constituted by repeating structures of disaccharides of galactose or galactose-6-O-sulfate and N-acetylglucosamine or N-acetylglucosamine-6-O-sulfate. Although the sulfate content varies depending on animal species, organs and so forth, those prepared from raw materials of cartilage, bone, cornea and so forth of cartilaginous fish such as shark, mammals such as whale and bovine can usually be used.

Keratan sulfate used as the raw material is not particularly limited and those usually available can be used. However, highly sulfated keratan sulfate, wherein galactose residues, which are constitutive saccharides, are sulfated is preferably used (highly sulfated keratan sulfate containing 1.5 to 2 sulfate groups per constitutive disaccharide may be referred to as keratan polysulfate). The sulfate group of the galactose residue is preferably located at the 6-position. Such highly sulfated keratan sulfate can also be obtained from, for example, proteoglycan of cartilaginous fish such as a shark. Those commercially available can also be used.

A keratan sulfate oligosaccharide obtained as described above of which sulfate group content is appropriately adjusted by a known method for desulfating or sulfating sugar chains may be used as the keratan sulfate oligosaccharide used in the present invention.

Substitution of an acyl group for a hydrogen atom of hydroxyl group in the keratan sulfate oligosaccharide can be performed by usual acylation methods employed for protection of hydroxyl groups of saccharides. For example, the acyl group can be introduced by allowing a keratan sulfate oligosaccharide to react with a reactive derivative of the acyl group to be introduced (carboxylic acid anhydride corresponding to the acyl group (for example, acetic anhydride when an acetyl group is introduced or propionic anhydride when a propanoyl group is introduced), acyl halide corresponding to the acyl group or the like) in an appropriate reaction solvent (pyridine, dioxane, tetrahydrofuran, N,N-dimethylformamide (DMF), acetonitrile, chloroform, dichloromethane, methanol, ethanol, water, mixtures thereof and so forth) in a conventional manner. If necessary, the reaction may be performed in the presence of a base catalyst such as pyridine.

If required, the degree of acylation can be adjusted. This adjustment can be attained by performing partial acylation in the aforementioned acylation method or partially removing acyl groups from the acylated keratan sulfate oligosaccharide.

Acyl groups can be removed by hydrolysis using methanolic ammonia, concentrated aqueous ammonia, sodium methoxide, sodium ethoxide, sodium hydroxide, potassium hydroxide or the like. The obtained derivative can be purified by reverse phase high performance liquid chromatography or the like.

The keratan sulfate oligosaccharide or a derivative thereof, which is an active ingredient of the inhibitor of the present invention, is preferably purified to such a degree that it can be used as a drug, and contains no such substances that are not accepted to be contained as drugs.

Since the inhibitor of the present invention is effective for inhibiting IL-12 production, diseases to which it is applicable are not limited so long as inhibition of IL-12 production is the purpose of administration. Examples of diseases against which inhibition of IL-12 production is effective include diseases that are caused by activation of Th1, where IL-12 accelerates progress of the diseases. Such diseases include, specifically, contact dermatitis, autoimmune uveoreinitis, allergic cerebrospinal meningitis, insulin dependent diabetes mellitus, diabetes mellitus, Hashimoto's disease, multiple sclerosis, rheumatoid arthritis, Sjögren's syndrome, Crohn's disease, ulcerative colitis, sarcoidosis, psoriasis, lipopolysaccharide-induced hepatonecrosis, crescentic glomerulonephritis, systemic lupus erythematosus and so on. Therefore, the inhibitor of the present invention encompasses a concept of an agent for treating these diseases as well.

The inhibitor of the present invention can be used not only with a purpose of genuine therapeutic treatment, but also with a purpose of prevention, maintenance (prevention of worsening), alleviation (improvement of conditions) of diseases and so forth.

In the present invention, an arbitrary dosage form can be appropriately selected depending on nature and progress of diseases, administration route and so forth.

The inhibitor of the present invention can be administered by injection (intravenous, intramuscular, subcutaneous, intracutaneous, intraperitoneal and so forth) or via nasal, oral or percutaneous route or by inhalation or the like. It can be appropriately formulated according to these administration routes. The dosage forms to be selected are not particularly limited, and can be selected from a wide range including, for example, injections (solution, suspension, emulsion, solid that can be dissolved upon use and so forth), tablet, capsule, granule, powder, liquid, liposome-encapsulated drug, ointment, plaster, lotion, paste, patch, gel, suppository, external powder, spray, inhaling powder and so forth. For preparation of these formulations, ingredients used for usual drugs (pharmaceutically acceptable carrier) such as conventional excipients, stabilizers, binders, lubricants, emulsifiers, osmotic regulators, pH regulators, coloring matters and disintegrating agents can also be used.

The formulating amount of the keratan sulfate oligosaccharide or a derivative thereof used as an active ingredient in the inhibitor of the present invention and the dose thereof are not particularly limited, but should be individually determined depending on the administration route, administration form, purpose of administration, and specific symptoms, body weight, age, sex of patients and so forth. As clinical dose of the keratan sulfate oligosaccharide, a single dose of 50 to 5000 mg per day for an adult is exemplified.

The safety of the keratan sulfate oligosaccharide, which is used as an active ingredient of the inhibitor of the present invention, is disclosed in International Publication WO96/16973. The safety of derivatives thereof can be inferred from the examples described later.

EXAMPLES

The present invention will be explained more specifically with reference to the following examples. However, the scope of the present invention should not be limited by these examples.

Example 1
Synthesis of Acetylated L4

Disodium salt of L4 (prepared by the method described in International Publication WO96/16973) was dissolved in deionized water, passed through a cation exchange resin column (Dowex 50W-X4, $H^+$-form: Dow Chemical) to make it into a free acid form, and immediately cooled with ice. The product was continuously maintained under ice cooling and tetra-n-butylammonium hydroxide diluted 10-fold with deionized water was added dropwise thereto in an amount of 1.1 equivalents for L4-sulfate groups. After stirring for about 1 hour, the solution was concentrated under reduced pressure at a low temperature, and passed through a Sephadex-LH20 column (Pharmacia) to be roughly purified. The obtained aqueous solution was lyophilized to obtain L4 di(tetra-n-butylammonium) salt.

The lyophilized L4 di(tetra-n-butylammonium) salt was dissolved in pyridine at a concentration of 100 mg/ml and acetic anhydride was added dropwise thereto in an amount of 1.5 equivalents with respect to the total hydroxyl groups in L4 at room temperature with stirring. After stirring at room temperature for 24 hours, the solvent was distilled off at a low temperature under reduced pressure, and the residue was reprecipitated repeatedly using a methanol/diethyl ether solvent system to obtain crude acetylated L4 di(tetra-n-butylammonium) salt. This salt was made into a sodium salt by anion exchange column chromatography (LiChroprep $NH_2$: Merck), purified by gel filtration chromatography (Cellulofine GCL-25: available from Seikagaku Corporation), and then lyophilized to obtain penta-O-acetylated L4 (hereafter also referred to as AcL4) represented by the formula (5) as a mixture of the compounds in α-glycoside configuration and β-glycoside configuration. The compounds in α-glycoside configuration and β-glycoside configuration were separated by anion exchange chromatography (LiChroprep RP-18: Merck) to obtain the compound in α-glycoside configuration. $^1$H-NMR spectrum and $^{13}$C-NMR (DEPT) spectrum of AcL4 (in α-glycoside configuration) are shown below.

$^1$H-NMR spectrum $^1$H-NMR (400 MHz, $D_2O$, TSP($\delta H$= 0.00 ppm)) $\delta_H$=1.97 ppm (s, 3H, $COCH_3$), 2.02 (s, 3H, $COCH_3$), 2.17 (s, 3H, $COCH_3$), 2.18 (s, 3H, $COCH_3$), 2.217 (s, 3H, $COCH_3$), 2.220 (s, 3H, $COCH_3$), 4.07–4.17 (m, 4H, H-4A, H-5A, H-6B, H-6'B), 4.22–4.28 (m, 3H, H-5B, H-6A, H-6'A), 4.40–4.44 (dd, 1H, H-2A), 4.91–4.93 (d, 1H, H-1B), 5.00–5.04 (dd, 1H, H-2B), 5.20–5.23 (dd, 1H, H-3B), 5.26–5.31 (dd, 1H, H-3A), 5.485–5.493 (d, 1H, H-4B), 6.09–6.10 (d, 1H, H-1A) $^{13}$C-NMR (DEPT) spectrum $^{13}$C-NMR (100MHz, $D_2O$, TSP($\delta_c$=0.00 ppm)) $\delta$hd c=22.86 ppm (2C, $OCOCH_3$), 23.04 ($OCOCH_3$), 23.08 ($OCOCH_3$), 23.43 ($OCOCH_3$), 24.47 ($NHCOCH_3$), 53.09 (C-2A), 67.98 (C-6B), 68.36 (C-6A), 70.61 (C-4B), 72.62 (C-2B), 73.34 (C-5B), 73.56 (2C, C-3A, C-5A), 74.27 (C-3B), 77.80 (C-4A), 93.38 (C-1A), 102.96 (C-1B) "A" represents an N-acetylglucosamine residue, and "B" represents a galactose residue.

Disodium salt of L4 (5 g) was dissolved in 50 ml of distilled water and passed through an Amberlite IR-120 (Sigma-Aldrich) column ($H^+$-form).

The pH of the combined solution of the acidic fractions was adjusted to 6.5 by addition of pyridine, then evaporated to remove excess of pyridine, lyophilized to obtain L4 dipyridinium salt.

L4 (disodium salt) and L4L4 (tetrasodium salt) used in the following examples were prepared by the method described in International Publication WO96/16973. L3 (monosodium salt) used was prepared by the following method.

5 g of dipyridinium salt of L4 was allowed to react in a mixed solution of acetyl chloride and methanol for desulfation. The solution after the reaction was applied to a Muromac column (Muromachi Kagaku Kogyo, 3×21 cm) equilibrated with distilled water. A NaCl concentration gradient of from 0 M (1L) to 2.0 M (1L) was applied on the column, and the eluent was collected as 16-ml fractions. The hexose content in each eluent fraction was measured to determine the eluted position of partially desulfated L4.

The fractions containing partially desulfated L4 were combined, concentrated under reduced pressure and deionized by a Sephadex G-10 column (Amersham Pharmacia Biotech) equilibrated with distilled water. The deionized preparation was lyophilized, then dissolved in 100 mM citrate/phosphate buffer containing 45 units of β-galactosidase (Seikagaku Corporation) and incubated at 37° C. for 45 hours to decompose the contained Galβ1-4GlcNAc(6S).

The reaction solution was applied to a Muromac column (3×32 cm) equilibrated with distilled water. A NaCl concentration gradient of from 0 M (1 L) to 1.5 M (1 L) was applied on the column, and the eluent was collected as 19-ml fractions. The hexose content in each eluent fraction was measured to determine the position of L3 elution.

The fractions containing L3 were combined, concentrated under reduced pressure and deionized by using a Sephadex G-10 column. As for the deionized L3 solution, salt exchange was performed to obtain sodium salt by using Dowex 59wx4 column (Dow Chemical), and the solution was applied again to a Muromac column (2.2×52 cm). A NaCl concentration gradient of from 0 M (1 L) to 0.75 M (1 L) was applied to the column, and the eluent was collected as 15-ml fractions. The eluent fractions were analyzed by capillary electrophoresis to determine the position of L3 elution.

After the fractions containing L3 were combined and NaCl was removed by using an electrodialysis apparatus (Micro Acilyzer, Asahi-kasei), the solution was concentrated to 5 ml under reduced pressure. The concentrated solution was applied as a portion of 400 μl (about 20 mg of L3) several times to a DAISO Pak column for high performance liquid chromatography (Daiso, 2×50 cm) equilibrated with 3 M NaCl and eluted with 3 M NaCl.

The eluted fractions containing L3 were combined, concentrated under reduced pressure, deionized by a Sephadex G-10 column (2.2×114 cm) equilibrated with distilled water, and then concentrated under reduced pressure again. The concentrated solution was filtered through an ultrafilter membrane (MW cutoff: 10,000) to remove endotoxins, lyophilized and used in the following examples.

Example 2
Decrease in Plasma IL-12 Caused by Administration of L4

Plasma IL-12 levels were examined using MRL-lpr/lpr mice treated with and without L4. Macrophages from MRL-lpr/lpr mice are known to markedly produce IL-12 and their serum IL-12 level is high (J. Exp. Med., 183, pp. 1447–1459 (1996)).

MRL lpr/lpr mice, C57BL/6 mice and ICR mice as normal controls were purchased from Japan Charles River Co., Ltd. and preliminarily maintained for several weeks before divided into groups. Blood was collected from the orbital venous plexus, and they were allocated according to the plasma creatinine level (CRE) as a first marker so that there would be no difference in the average value and the standard deviation for the creatinine level among the groups. They were also grouped so that there would be no difference in the plasma nitrogen level (BUN), white blood cell count (WBC), platelet count (PLT) and weight between groups as far as possible.

Groups used were as follows.

TABLE 1

| Group | Animal | Test substance | Dose (mg/kg) | Concentration (mg/ml) | Volume (ml/kg) | Route | No. of animals (male) | Duration |
|---|---|---|---|---|---|---|---|---|
| 1 | MRL | DW | — | — | 5.0 | p.o. | 9 | 4 weeks |
| 2 | MRL | L4 | 1.6 | 16 | 0.1 | i.n. | 9 | 4 weeks |
| 3 | MRL | L4 | 80 | 16 | 5.0 | p.o. | 9 | 4 weeks |
| 4 | MRL | L4 | 160 | 32 | 5.0 | p.o. | 9 | 4 weeks |
| 5 | C57BL/6 | Untreated | — | — | — | | 6 | — |
| 6 | ICR | Untreated | — | — | — | | 6 | — |

DW = distilled water, p.o. = oral administration, i.n. = intranasal (nasal mucosa) administration The test substances were administered from the next day of the grouping. Each of the test substances was dissolved in distilled water at a predetermined concentration to prepare a solution to be administered. The solution was intermittently administered 3 times per week for 4 weeks (total 12 doses).

Oral administration was performed by using 1-ml sterilized disposable syringe and a sterilized oral sonde in a conventional manner. Intranasal administration was performed by using a micropipette and a sterilized chip in a conventional manner.

Observation and measurement were performed as described below.

(1) General Conditions

General conditions and death of the mice were investigated every day once or more per day during the observation period of 29 days from the start of administration through the autopsy.

(2) Body Weight

Body weight was measured at the time of the grouping, on the first day of administration and thereafter every week.

(3) Hematological Test

Blood was collected from the orbital venous plexus at the time of the grouping and on the day before the autopsy. The white blood cell count (WBC) was measured by using an automatic cytometer for multiple test items (Sysmex K-2000: Toa Medical Electronics).

(4) Autopsy

Autopsy was performed when the final observation was completed. Presence or absence of abnormalities in major organs was investigated. Weights of liver, kidney, spleen, mesentery and cervical lymph node were also measured. Autopsy was similarly performed for mice that had died during the test.

(5) Blood Cytokine

Blood was collected from the orbital venous plexus at the time of the grouping and on the day before the autopsy. The IL-12 concentration in blood plasma was measured by using an IL-12 p70 ELISA kit (Endogen, Inc.).

The average value and the standard deviation were calculated for the measured values obtained as above and the statistical significance was analyzed by Williams' multiple comparison test.

The results were as follows.

(1) General Conditions

No change was observed.

(2) Body Weight

Favorable transition was observed in all of the groups.

(3) Hematological Test

In the low dose L4 administered groups, significant inhibition of the increase in WBC was observed. FIG. 1 shows the results of the groups 1, 2, 3 and 4 on the day before autopsy. In the figure, * indicates that there was statistical significance at a level of p<0.05.

(4) Autopsy

No abnormality was observed. No significant difference was observed for the organ weights, either.

(5) Blood Cytokine

Figure 2:
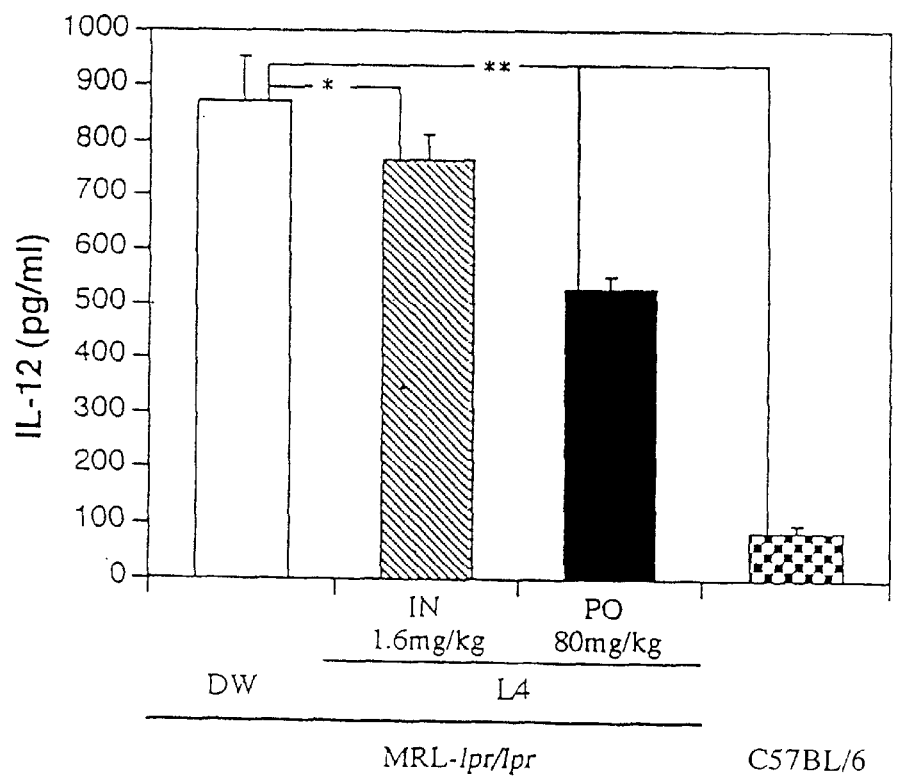
FIG. 2 shows the IL-12 level in plasma of MRL-lpr/lpr mice after administration of L4.

In the L4-administered groups, significant inhibition of the increase in IL-12 was observed. FIG. 2 shows the results of the groups 1, 2, 3 and 5 on the day before the autopsy. In the figure, * and ** indicate that there was statistical significance at levels of p<0.05 and p<0.01, respectively. The group 5 (C57BL/6 mice) represents the level of normal mice.

These results demonstrated that L4 had an action to inhibit IL-12 production.

Example 3
Effect of Administration of Acetylated L4

9-Week old MRL lpr/lpr mice, C57BL/6 mice and ICR mice were purchased from Japan Charles River Co., Ltd. and preliminarily maintained for 6 weeks before divided into groups. The groups used were as follows.

TABLE 2

| Group | Animal | Test substance | Dose (mg/kg) | Concentration (mg/ml) | Volume (ml/kg) | Route | No. of animals (female) | Duration |
|---|---|---|---|---|---|---|---|---|
| 1 | MRL | DW | — | — | 5.0 | p.o. | 9 | 6 weeks |
| 2 | MRL | AcL4 | 2.0 | 0.4 | 5.0 | p.o. | 9 | 6 weeks |
| 3 | MRL | AcL4 | 4.0 | 0.8 | 5.0 | p.o | 9 | 6 weeks |
| 4 | MRL | AcL4 | 8.0 | 1.6 | 5.0 | p.o. | 9 | 6 weeks |
| 5 | MRL | L4 | 3.2 | 32.0 | 0.1 | i.n. | 9 | 6 weeks |
| 6 | C57BL/6 | Untreated | — | — | — | | 6 | — |
| 7 | ICR | Untreated | — | — | — | | 6 | — |

DW = distilled water, AcL4 = acetylated L4, p.o. = oral administration, i.n. = intranasal (nasal mucosa) administration Each of the test substance was dissolved in distilled water at a predetermined concentration to prepare a solution to be administered. The solution was intermittently administered 3 times per week for 6 weeks (total 19 doses). Observation was performed for 45 days from the start of administration through the autopsy. Other conditions and methods were the same as those of Example 2.

Figure 3:
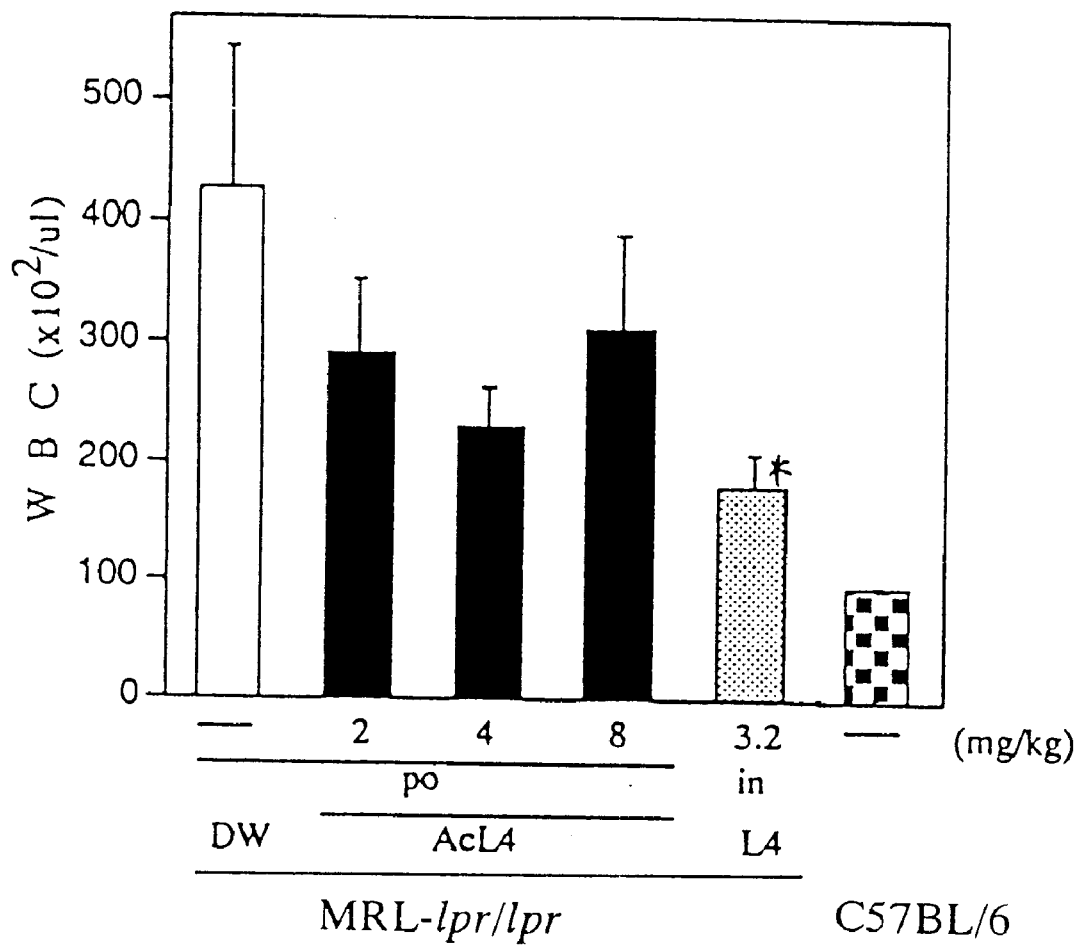
FIG. 3 shows counts of WBC in blood of MRL-lpr/lpr mice after administration of L4.

The results were as follows.
(1) General Conditions
No change was observed.
(2) Body Weight
Favorable transition was observed in all of the groups.
(Hematological Test
In the L4-intranasally-administered group and the acetylated L4-administered groups, significant inhibition of the increase in WBC was observed. FIG. 3 shows the results of the groups 1 to 6 on the day before the autopsy. In the figure, * indicates that there was statistical significance at a level of $p<0.05$.
(4) Biochemical Blood Test
Blood was collected from the orbital venous plexus and plasma creatinine level (CRE) and plasma urea nitrogen level (BUN) were measured by using an automatic analyzer for clinical chemistry (COBAS MIRA S: Nippon Roche) at the time of the grouping and on the day before the autopsy.

Figure 4:
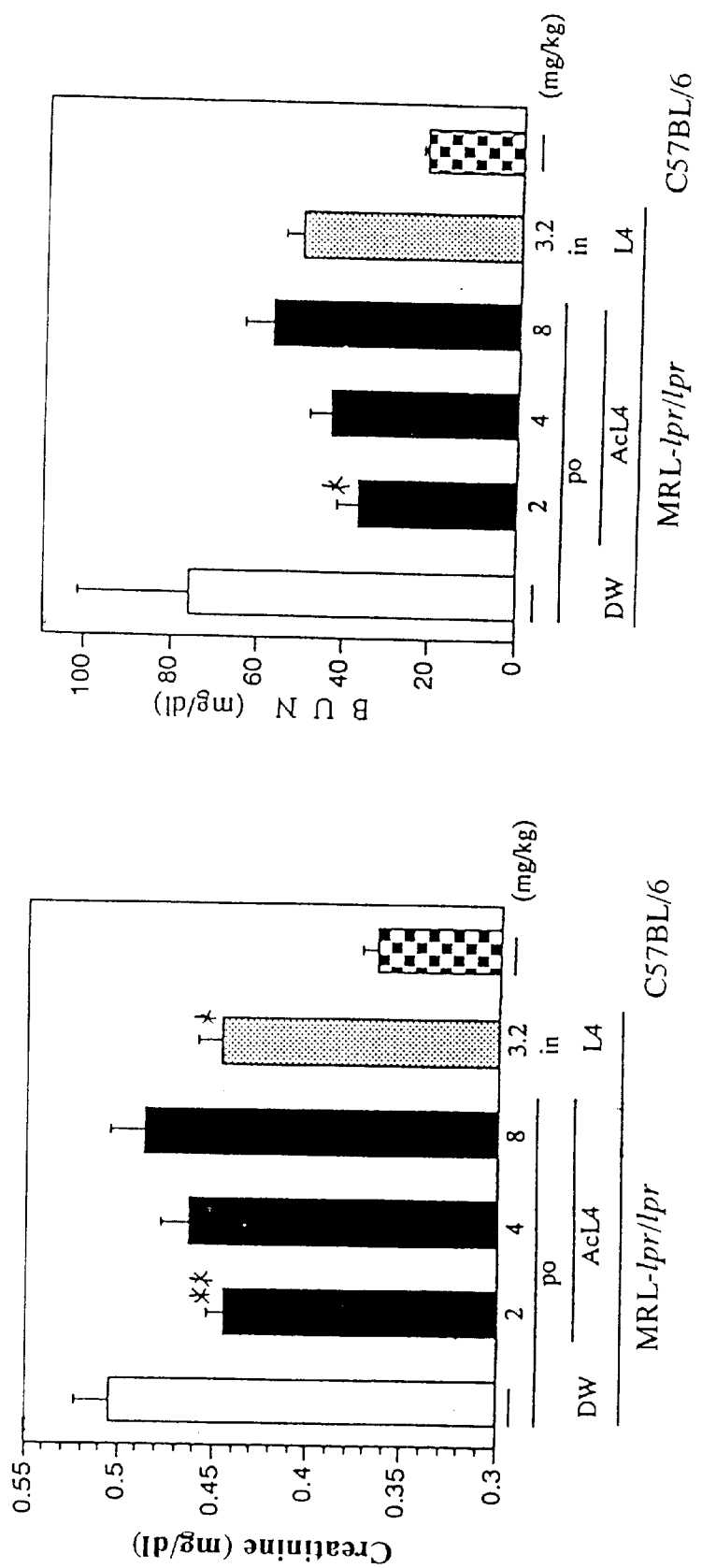
FIG. 4 shows plasma CRE and BUN levels of MRL-lpr/lpr mice after administration of L4.

As a result, in the acetylated L4-administered groups and the L4-administered group, significant decrease in CRE and BUN was observed. FIG. 4 shows the results of the groups 1 to 6 on the day before autopsy. In the figure, * and ** indicate that there was statistical significance at levels of $p<0.05$ and $p<0.01$, respectively.

Figure 5:
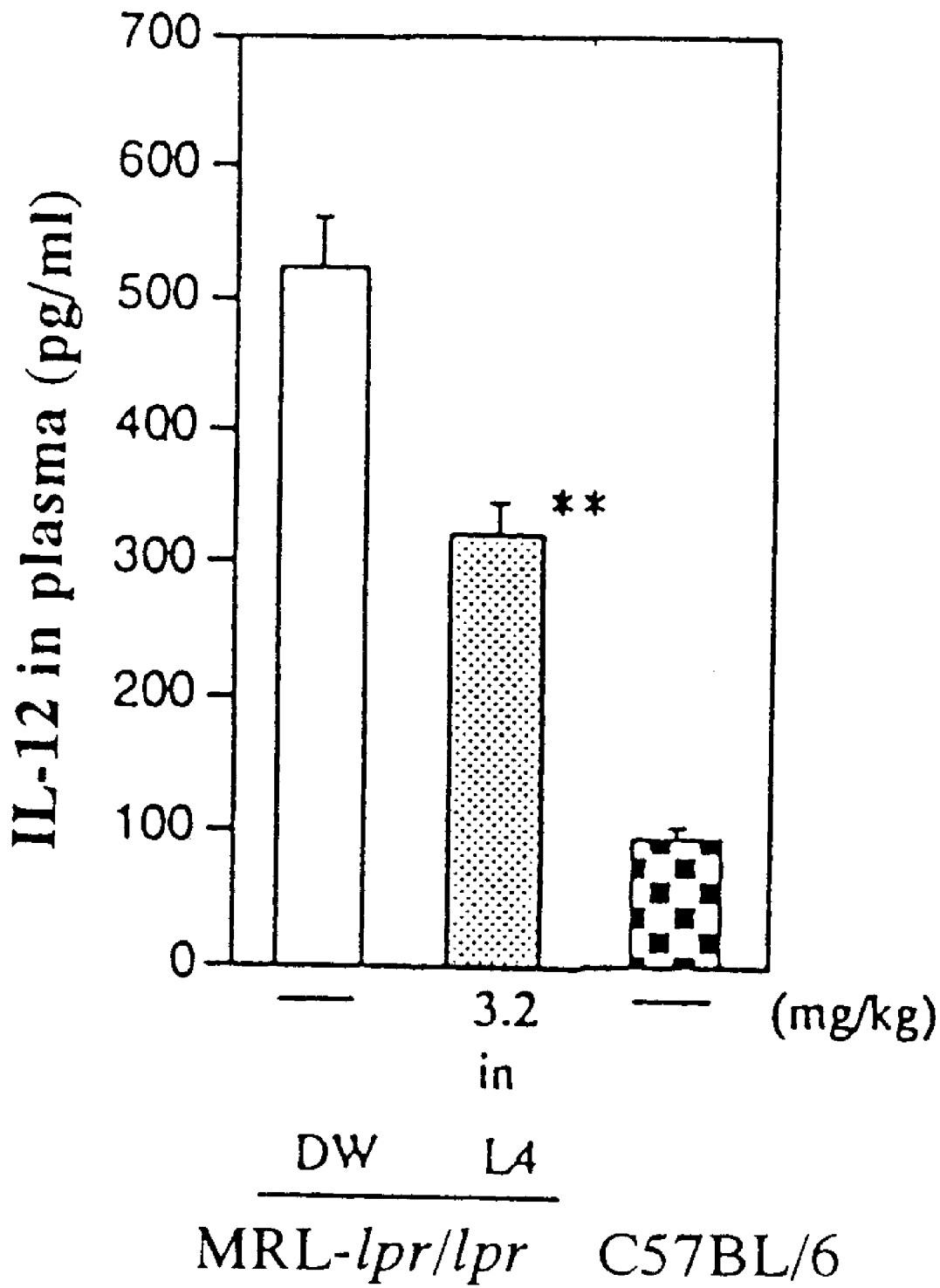
FIG. 5 shows the IL-12 level in plasma of MRL-lpr/lpr mice after administration of L4.

These results demonstrated that L4 and acetylated L4 were useful as therapeutic and prophylactic agents for renal diseases (for example, nephritis (glomerulonephritis etc.), nephropathy (lupus nephropathy etc.)).
(5) Autopsy
No abnormality was observed. No significant difference was observed in the organ weights, either.
(6) Blood Cytokine
In the L4-intranasally-administered group, significant inhibition of the increase in the IL-12 was observed. FIG. 5 shows the results of the groups 1, 5 and 6 on the day before the autopsy. In the figure, ** indicates that there was statistical significance at a level of $p<0.01$.

It was also confirmed from these results that L4 had an action to inhibit IL-12 production.

Example 4
Decrease in IL-12 p70 Production in Macrophages Caused by L4 Treatment Five to seven milliliters of ice-cooled Hank's balanced salt solution was injected in the abdominal cavities of 8- to 39-week-old MRL lpr/lpr mice and extracted 5 minutes later to collect resident peritoneal cells. The collected cells were cultured overnight in RPMI medium contained in a 96-well flat-bottom plate at 37° C. in the presence of 5% $CO_2$. After the cultivation, non-adherent cells were removed and adherent cells were used as peritoneal macrophages for the experiment.

The cells were treated with lipopolysaccharide (LPS, List Biological Laboratories, Inc.) for 24 hours to stimulate IL-12 production. The concentration of IL-12 p70 in the cell culture supernatant was measured by using an IL-12 p70 ELISA kit (Endogen, Inc.) to evaluate the IL-12 production. As for the measured values, the average value and the standard deviation were obtained. Unless otherwise mentioned, the statistical significance was examined by the Williams' multiple comparison test.

The experiment will be explained below.
(1) Simultaneous Treatment with LPS and L4
The stimulation was performed for 24 hours in the medium containing LPS (100 ng/ml) and various concentrations of L4, and then the IL-12 production was evaluated.
(2) Treatment with L4 After Preliminary Stimulation with LPS
Macrophages were treated with 100 ng/ml of LPS for 0, 2 or 6 hours, and then the medium was replaced with a fresh medium containing 1000 ng/ml of L4 or a fresh medium only (L4(-)) (consequently, IL-12 produced by the pretreatment was removed). 24 hours after the replacement of the medium, the IL-12 production was evaluated.
(3) Stimulation with LPS After Pretreatment with L4
First, macrophages were treated with L4 at various concentrations for 24 hours and the medium was replaced with a medium containing 100 ng/ml of LPS. 24 hours after the replacement of the medium, the IL-12 production was evaluated.

Figure 6:
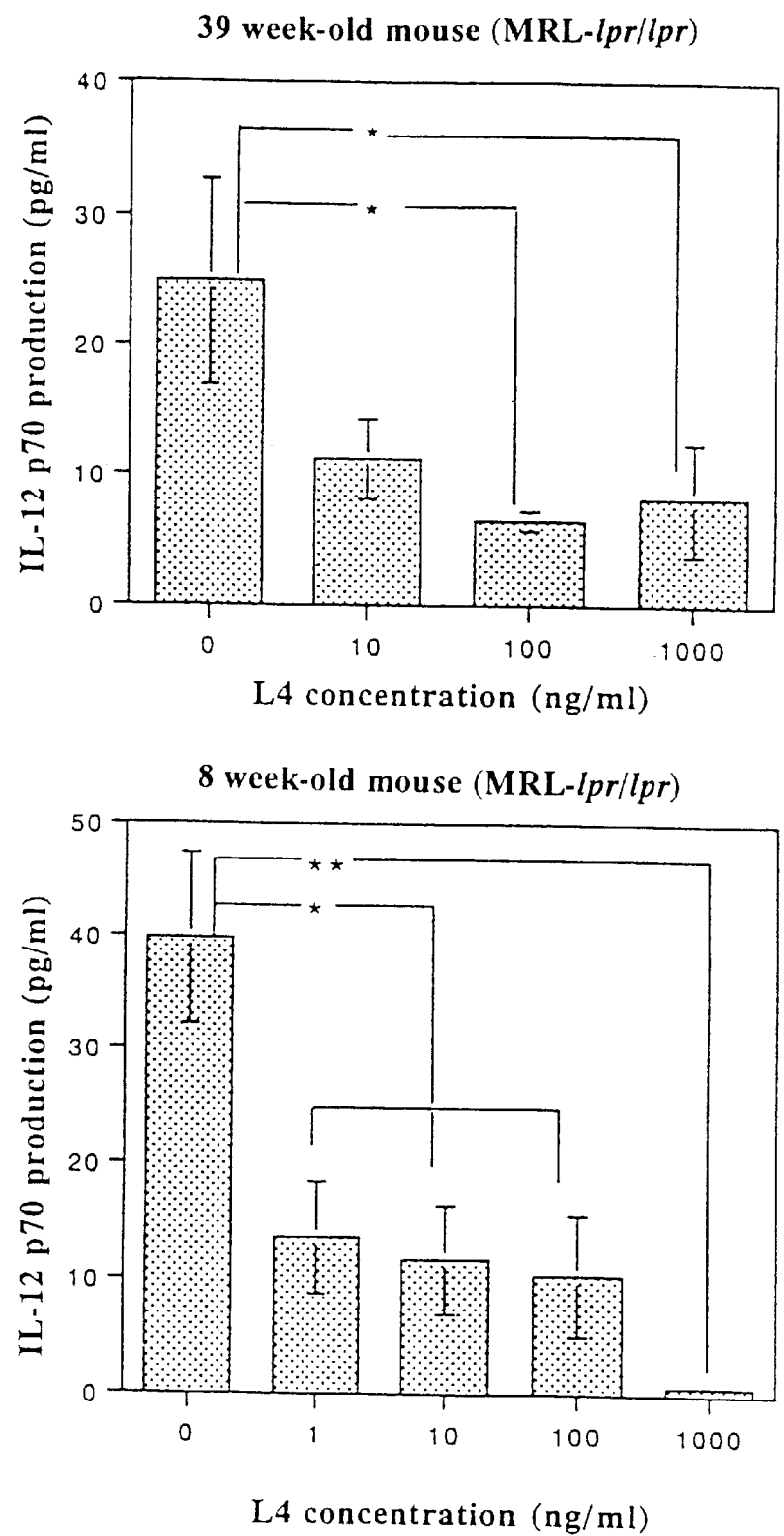
FIG. 6 shows the inhibitory effect of L4 on the IL-12 p70 production in peritoneal macrophages isolated from 8-week old and 39-week old MRL mice.
Figure 7:
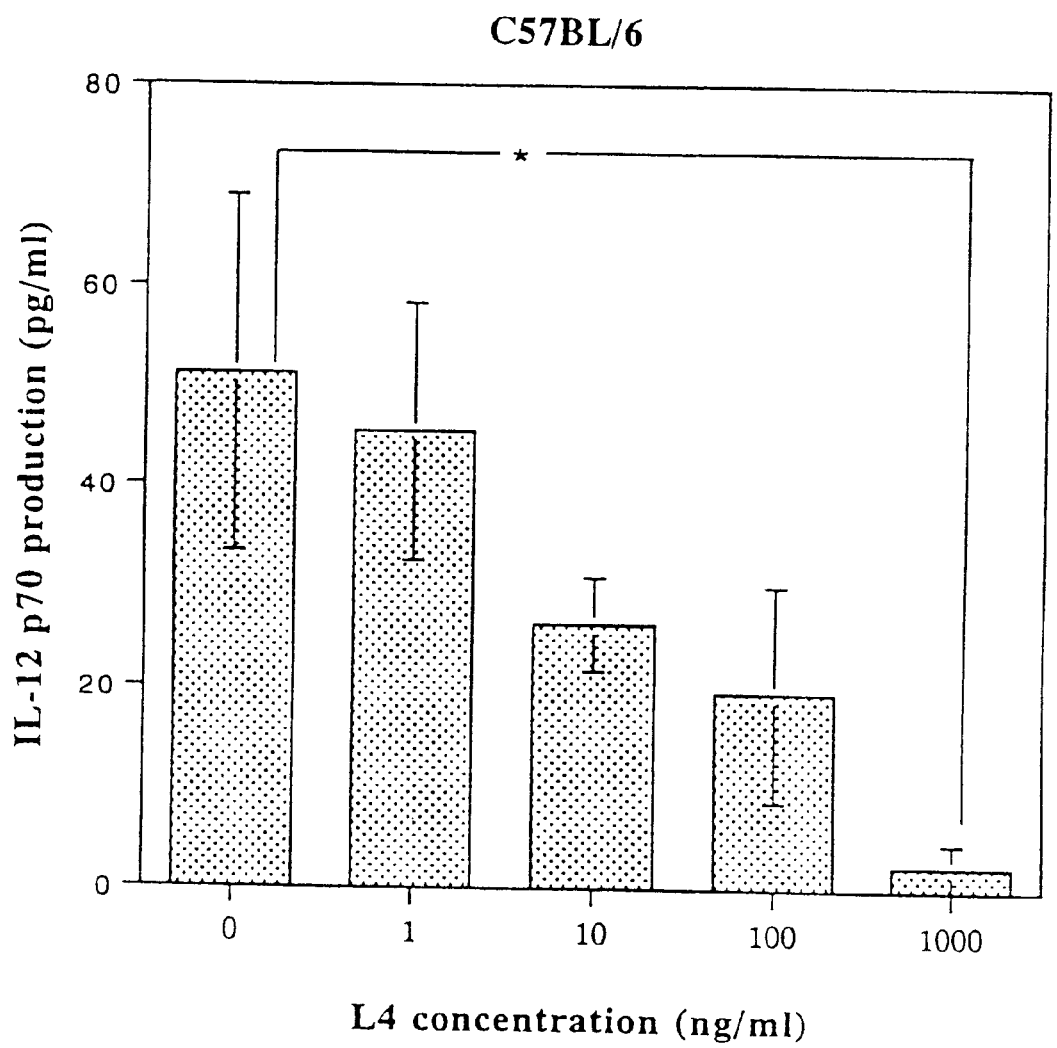
FIG. 7 shows the inhibitory effect of L4 on the IL-12 p70 production in peritoneal macrophages isolated from C57BL6/7 mice.

The results of simultaneous treatment with LPS and L4 are shown in FIG. 6. In the groups that were stimulated with 100 ng/ml LPS, L4 showed dose-dependent inhibitory effect on the IL-12 production. The same result was obtained for both of 8-week-old mice and 39-week-old mice (FIG. 6). The same result was also obtained when other types of mice (C57BL/6 mice) were used (FIG. 7). In FIGS. 6 and 7, * and ** indicate that there was statistical significance at levels of $p<0.05$ and $p<0.01$, respectively.

Figure 8:
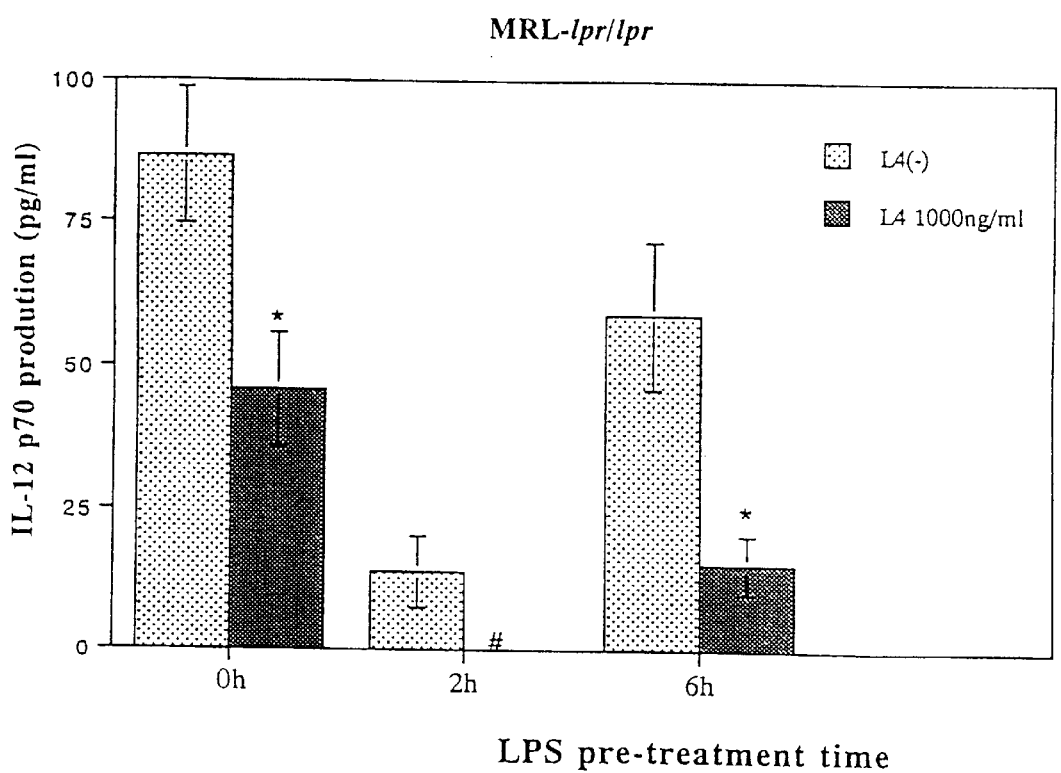
FIG. 8 shows the inhibitory effect of L4 on the IL-12 p70 production in peritoneal macrophages isolated from MRL mice.

The results obtained when macrophages were treated with L4 after the preliminary stimulation with LPS are shown in FIG. 8. In the figure, # indicates that detection was not possible. * indicates that there was statistical significance at a level of $p<0.05$ according to the Student's t-test. Inhibition of the IL-12 production by L4 was also observed in macrophages pretreated with LPS for 2 and 6 hours.

These results demonstrated that L4 could inhibit IL-12 production even after stimulation with LPS.

Figure 9:
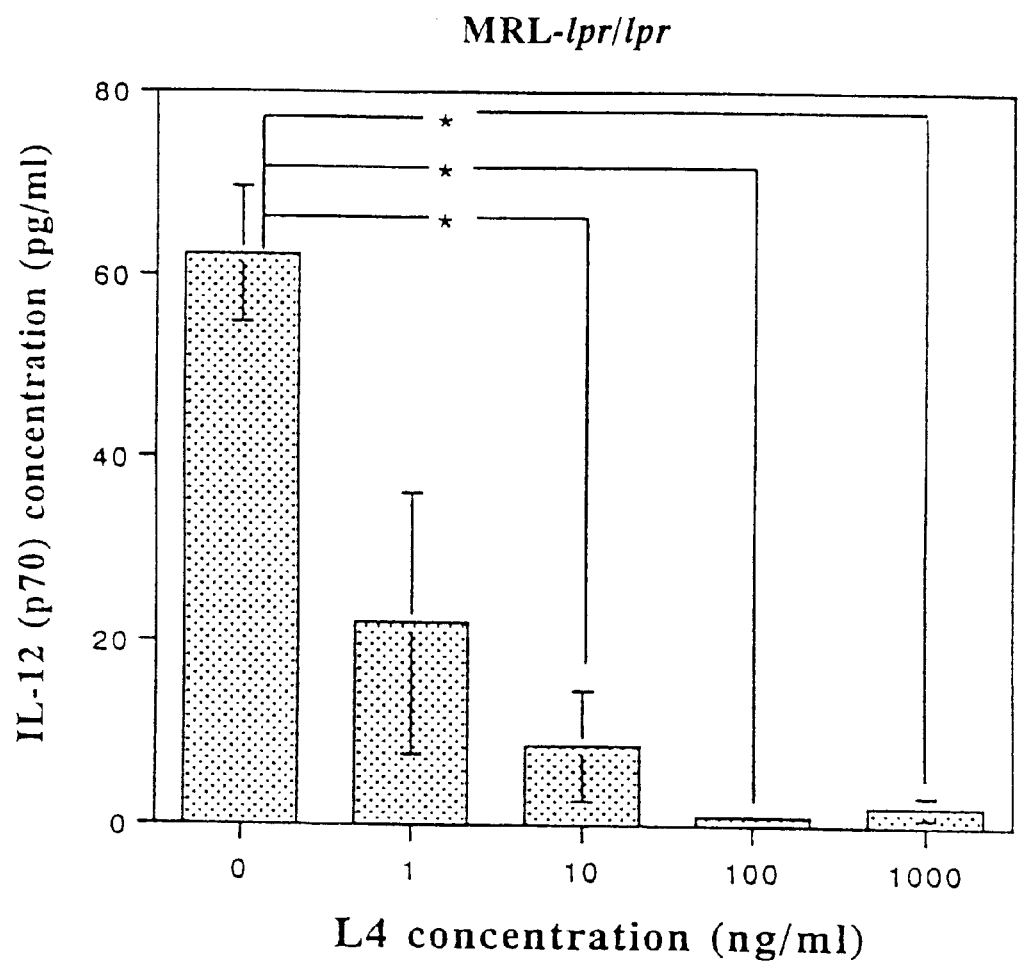
FIG. 9 shows the inhibitory effect of L4 on the IL-12 p70 production in peritoneal macrophages isolated from MRL mice.
Figure 10:
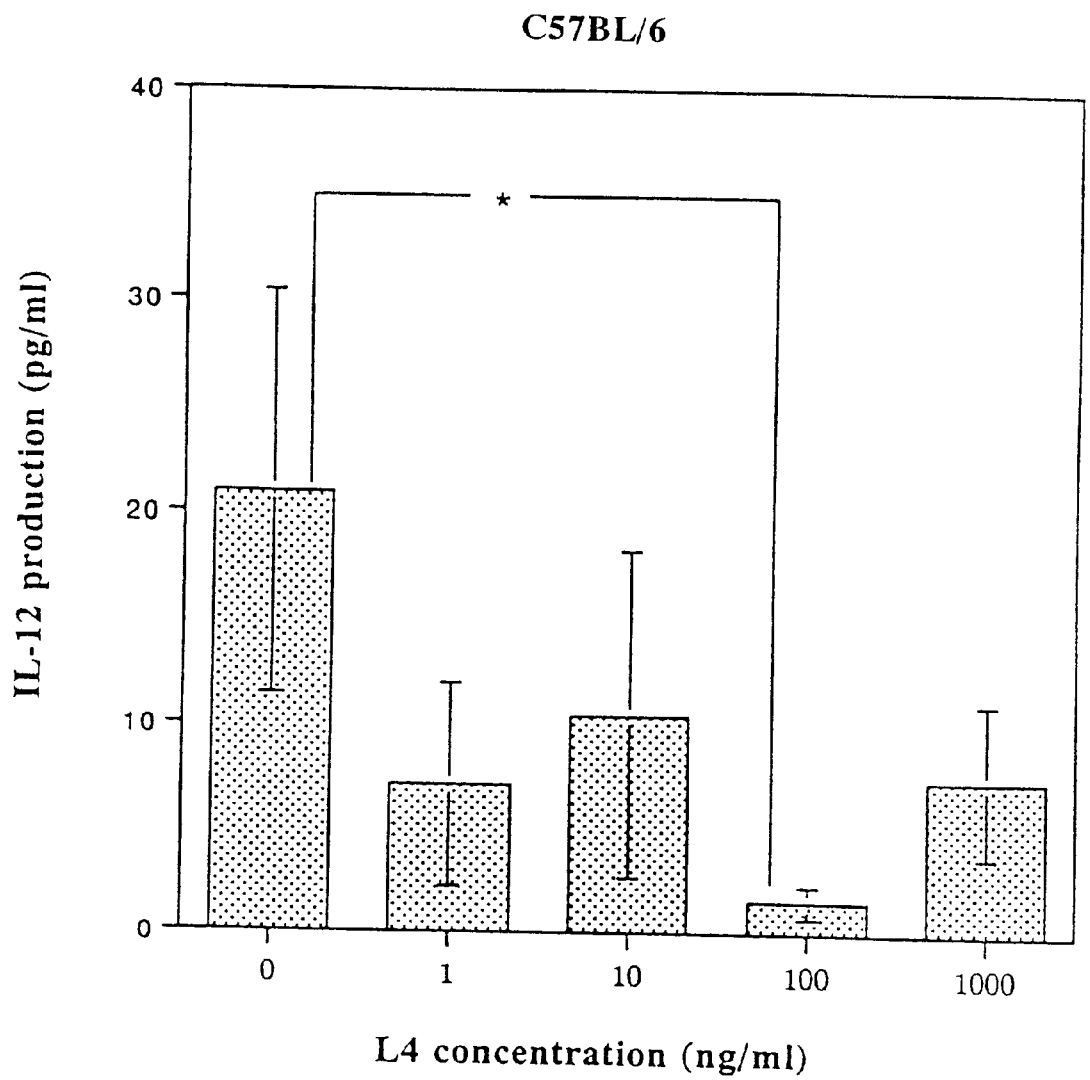
FIG. 10 shows the inhibitory effect of L4 on the IL-12 p70 production in peritoneal macrophages isolated from C57BL6/7 mice.

The results obtained when macrophages were stimulated with LPS after the pretreatment with L4 are shown in FIG. 9. In the figure, * indicates there was statistical significance at a level of $p<0.05$. It is evident that L4 pretreatment inhibits the IL-12 production. The IL-12 production was almost completely inhibited at high doses (100 ng/ml or more). The same results were also obtained when other normal mice (C57BL/6 mice) were used (pretreated with L4 for 36 hours) (FIG. 10). In FIG. 10, * indicates that there was statistical significance at a level of $p<0.05$.

Figure 11:
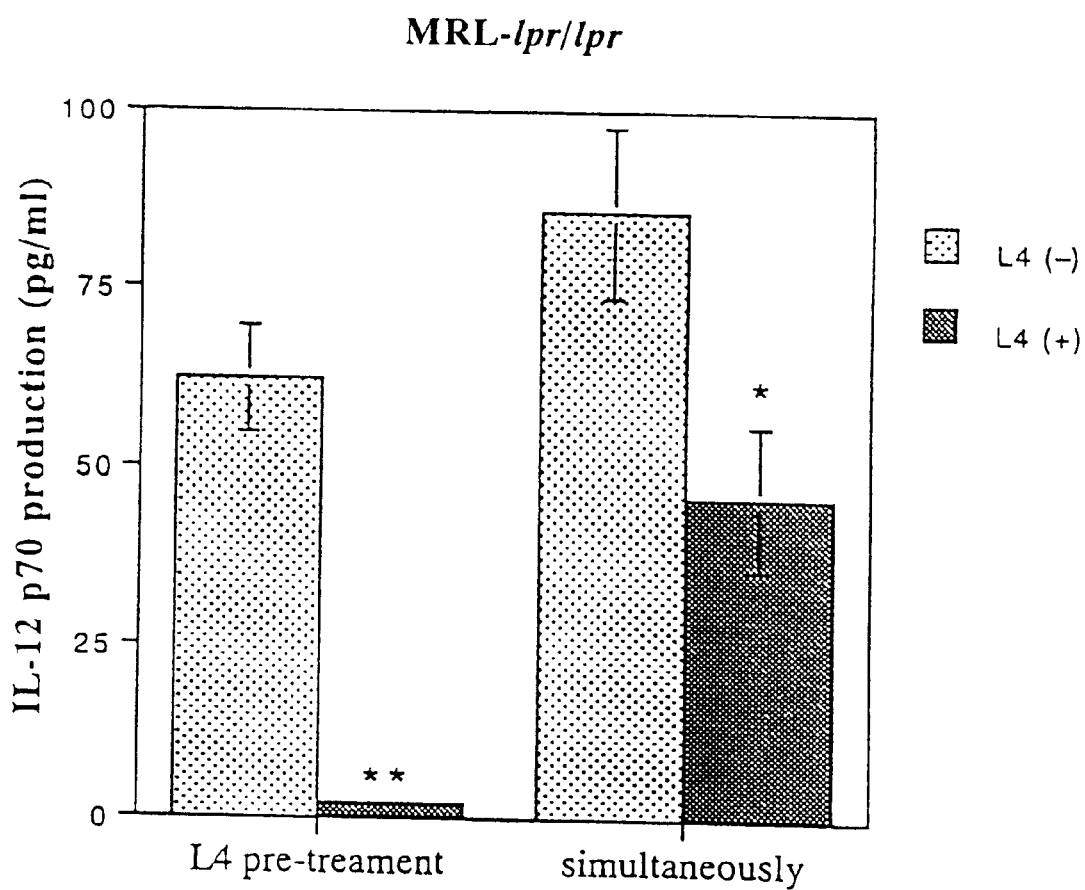
FIG. 11 shows the inhibitory effect of L4 on the IL-12 p70 production in peritoneal macrophages isolated from MRL mice.

The IL-12 production in the macrophages of MRL-lpr/lpr mice, pretreated with or without 1000 ng/ml of L4 for 24 hours then treated with 100 ng/ml of LPS for 24 hours (L4 pretreatment), and the treated with 100 ng/ml LPS together with or without 1000 ng/ml of L4 (simultaneous treatment), were compared. The results are shown in FIG. 11. In FIG. 11, * and ** indicate that there was statistical significance at levels of $p<0.05$ and $p<0.01$, respectively, according to the Student's t-test.

From the data shown in FIG. 11, it can be seen that L4 pretreatment inhibits IL-12 production more efficiently compared with the simultaneous treatment.

Figure 12:
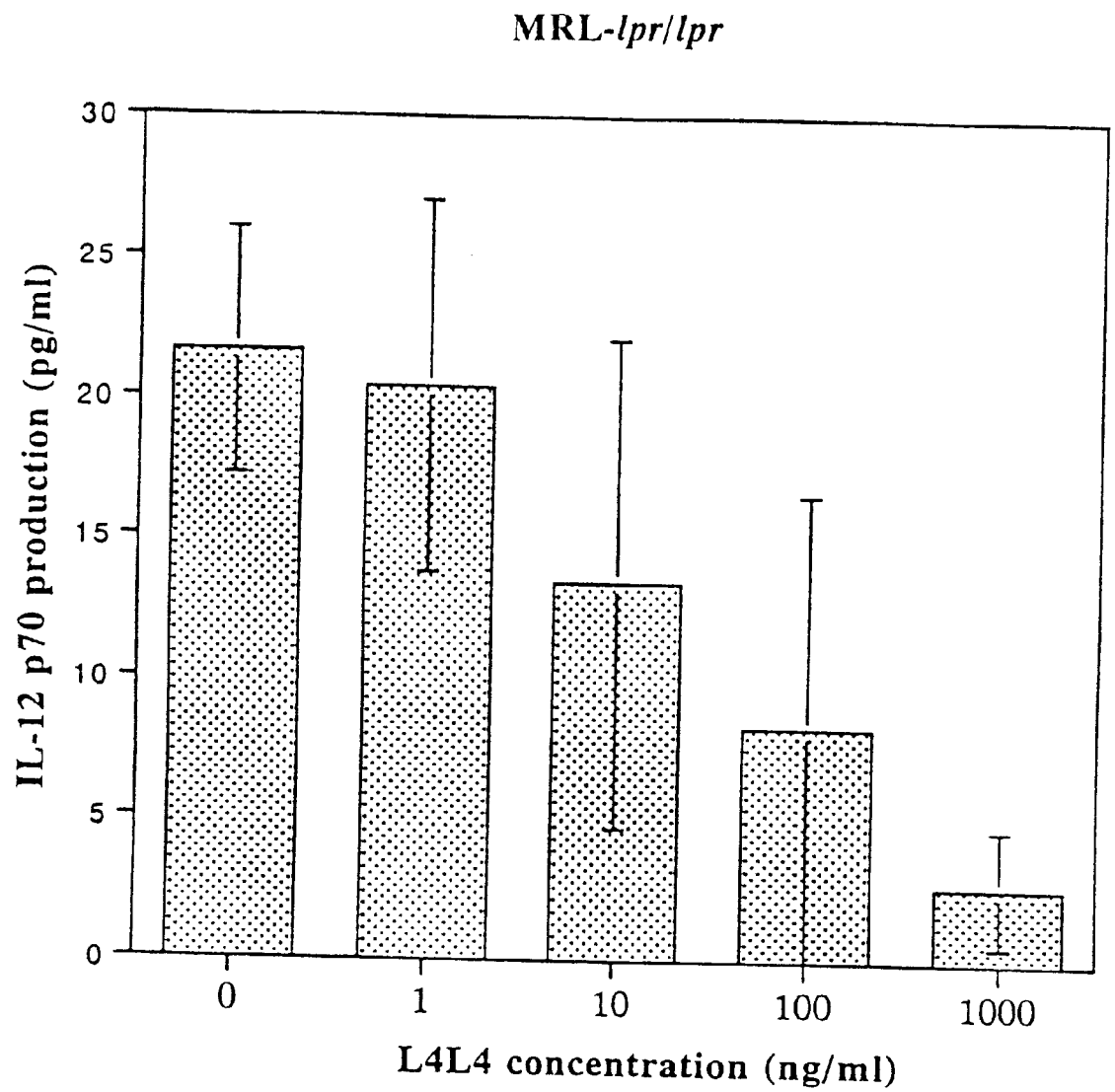
FIG. 12 shows the inhibitory effect of L4L4 on the IL-12 p70 production in peritoneal macrophages isolated from MRL mice.

The same result was obtained when L4L4 (tetrasodium salt) was used instead of L4. The results of stimulation with 100 ng/ml of LPS for 24 hours in the presence of L4L4 at various concentrations are shown in FIG. 12.

Example 5
Decrease in IL-12 p70 Production Caused by L4 Treatment in Synovial Cells from Rheumatoid Arthritis Patients A cell suspension was prepared by suspending synovial cells collected from human rheumatoid arthritis patients in RPMI1640 medium (Sigma) containing 500 ng/ml of LPS, 50 U/ml of recombinant mouse interferon-γ (IFN-γ) and 10% fetal bovine serum at a concentration of $1 \times 10^6$ cells/ml.

100 μl of the aforementioned cell suspension was dispensed to a 96-well flat-bottom plate and further 100 μl of L4 solution of which concentration was adjusted to be twice the final concentration in the RPMI1640 medium was added thereto. Then, the cells were cultured at 37° C. in the presence of 5% $CO_2$ for 24 hours.

Subsequently, the plate was centrifuged to collect the culture supernatant. The IL-12 concentration in the supernatant was measured as described above. The results are shown in FIG. 13.

Figure 13:
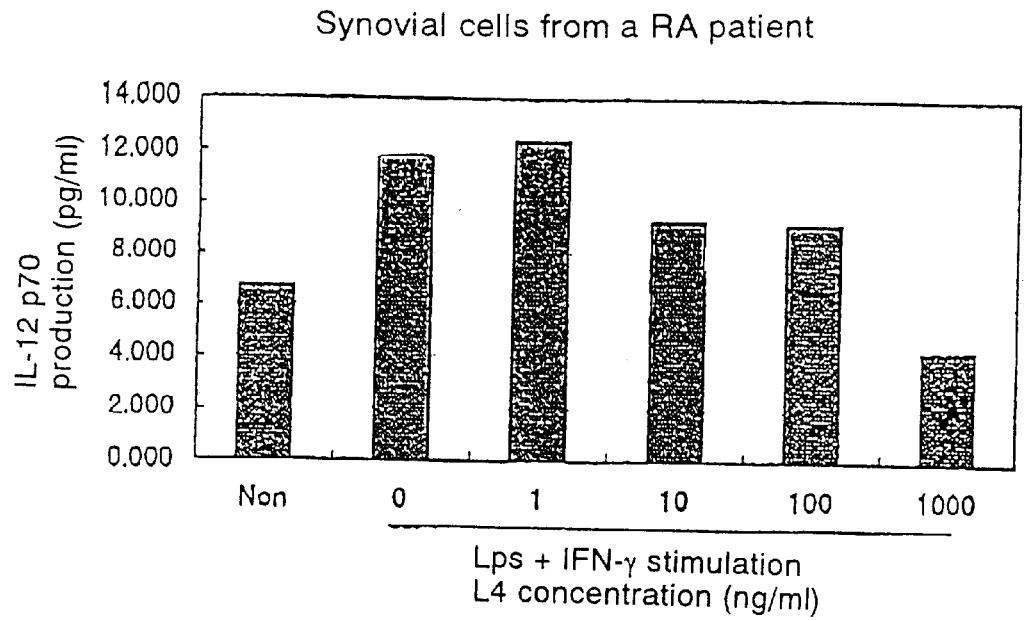
FIG. 13 shows the inhibitory effect of L4 on the IL-12 p70 production in synovial cells isolated from human chronic rheumatoid arthritis patients.

As shown in FIG. 13, there was observed a tendency that addition of L4 inhibited IL-12 production. The IL-12 production in synovial cells was almost halved by 1000 ng/ml L4.

Example 6
Decrease in IL-12 p40 Production Caused by L3 Treatment in Macrophages Ice-cooled phosphate buffered saline (PBS) was injected into abdominal cavities of C3H/HeN mice. After the abdomen of each mouse was massaged, the PBS was collected and centrifuged to obtain macrophages. A cell suspension was prepared by suspending the obtained macrophages in RPMI1640 medium (Sigma) containing 200 ng/ml of LPS, 2 U/ml of recombinant mouse interferon-γ (IFN-γ) and 10% fetal bovine serum at a concentration of $1 \times 10^6$ cells/ml. 100 μl of the cell suspension was dispensed on a 96-well flat-bottom plate and further 100 μl of L3 solution of which concentration was adjusted to be twice the final concentration in the RPMI1640 medium was added thereto. Then, the cells were cultured at 37° C. in the presence of 5% $CO_2$ for 24 hours.

Subsequently, the plate was centrifuged to collect the culture supernatant. The IL-12 concentration in the supernatant was measured as described above. The results are shown in FIG. 14.

Figure 14:
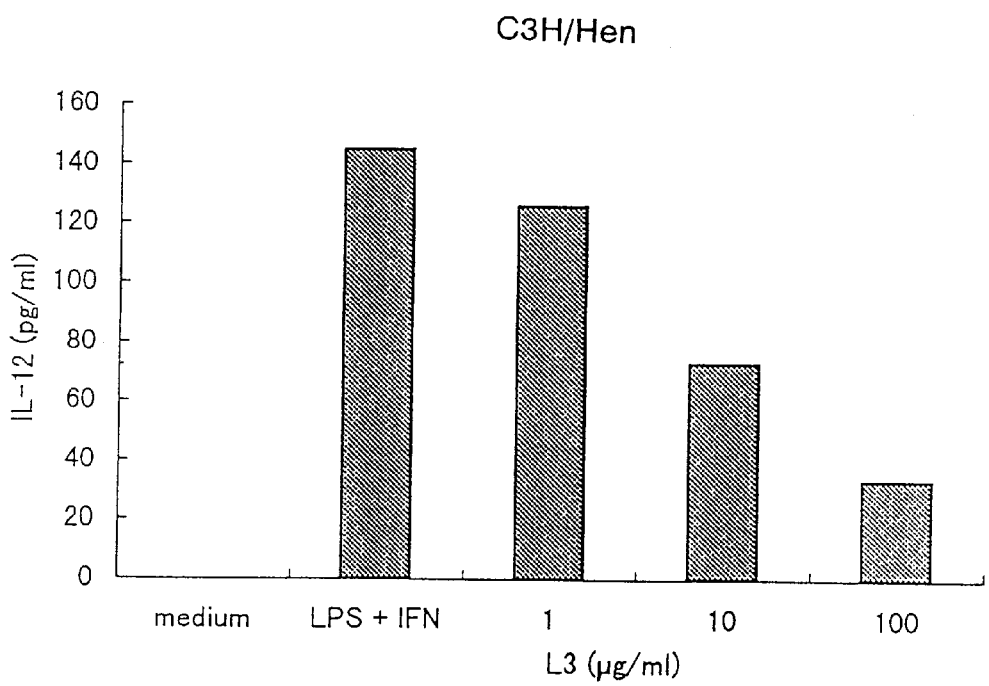
FIG. 14 shows the inhibitory effect of L3 on the IL-12 p70 production in peritoneal macrophages isolated from C3H/HeN mice.

As is evident from the results shown in FIG. 14, L3 inhibited IL-12 production of macrophages in a dose-dependent manner.

The data from Examples 2 to 6 clearly indicate that the keratan sulfate oligosaccharide or derivatives thereof can inhibit IL-12 production. In particular, it is evident that preliminary administration of the substances can inhibit the IL-12 production thereafter (i.e., they have a preventive effect).

What is claimed is:

1. A pharmaceutical composition for inhibiting IL-12 production, which comprises an acyl ester at a hydroxyl group of a keratan sulfate oligosaccharide and a pharmaceutically acceptable carrier.

2. The composition according to claim 1, wherein the keratan sulfate oligosaccharide comprises at least one repeating unit of either one of the disaccharides represented by the following formulas:

Gal(6S)-GlcNAc(6S) and Gal(6S)-GlcNAc wherein Gal represents a galactose residue, GlcNAc represents an N-acetylglucosamine residue, 6S indicates that 6-O-sulfate ester is formed at a hydroxyl group at the 6-position, and - represents a glycosidic linkage.

3. The composition according to claim 2, wherein the keratan sulfate oligosaccharide is selected from those represented by the formulas (1) to (3):

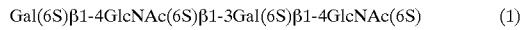

Gal(6S)β1-4GlcNAc(6S)β1-3Gal(6S)β1-4GlcNAc(6S)    (1)

Gal(6S)β1-4GlcNAc(6S)    (2)

Gal(6S)β1-4GlcNAc    (3)

wherein Gal represents a galactose residue, GlcNAc represents an N-acetylglucosamine residue, 6S indicates that 6-O-sulfate ester is formed at a hydroxyl group at the 6-position, β1-4 represents a β-1,4-glycosidic linkage and β1-3 represents a β-1,3-glycosidic linkage.

4. The composition according to claim 1, wherein the acyl ester is represented by the following formula (4):

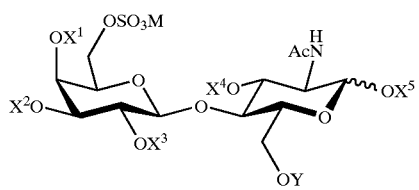 (4)

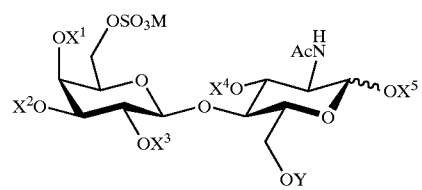 (4)

wherein $X^1$ to $X^5$ each independently represent a hydrogen atom or an acyl group, provided that at least one of $X^1$ to $X^5$ is an acyl group; Y is a hydrogen atom or $SO_3M$; M is independently a hydrogen atom, or a monovalent to trivalent metal or a monovalent to trivalent base that may be ionized; and the linkage represented by a wavy line represents a linkage in α-glycoside configuration or β-glycoside configuration.

5. The composition according to claim 4, wherein each of $X^1$ to $X^5$ represents an acyl group having 1 to 10 carbon atoms and M is an alkali metal.

6. A keratan sulfate oligosaccharide derivative represented by the following formula (4):

wherein $X^1$ to $X^5$ each independently represent a hydrogen atom or an acyl group, provided that at least one of $X^1$ to $X^5$ is an acyl group; Y is a hydrogen atom or $SO_3M$; M is independently a hydrogen atom, or a monovalent to trivalent metal or a monovalent to trivalent base that may be ionized; and the linkage represented by a wavy line represents a linkage in α-glycoside configuration or β-glycoside configuration.

7. The derivative according to claim 6, wherein each of $X^1$ to $X^5$ represents an acyl group having 1 to 10 carbon atoms and M is an alkali metal.

8. A method for inhibiting IL-12 production, comprising administering an effective amount of an acyl ester at a hydroxyl group of a keratan sulfate oligosaccharide to a subject in need of inhibition of IL-12 production.

* * * * *